(12) United States Patent
Ozturk et al.

(10) Patent No.: US 11,543,429 B2
(45) Date of Patent: Jan. 3, 2023

(54) NANOSCALE SCANNING ELECTROCHEMICAL MICROSCOPY ELECTRODE METHOD

(71) Applicant: Morgan State University, Baltimore, MD (US)

(72) Inventors: Birol Ozturk, Parkville, MD (US); Alperen Guver, Baltimore, MD (US); Peker Milas, Baltimore, MD (US)

(73) Assignee: Morgan State University, Baltimore, MD (US)

( * ) Notice: Subject to any disclaimer, the term of this patent is extended or adjusted under 35 U.S.C. 154(b) by 284 days.

(21) Appl. No.: 16/857,821

(22) Filed: Apr. 24, 2020

(65) Prior Publication Data

US 2020/0341029 A1    Oct. 29, 2020

Related U.S. Application Data

(60) Provisional application No. 62/838,474, filed on Apr. 25, 2019.

(51) Int. Cl.
| | | |
|---|---|---|
| *G01Q 60/60* | (2010.01) | |
| *G01Q 70/12* | (2010.01) | |
| *C12Q 1/00* | (2006.01) | |
| *G01N 33/543* | (2006.01) | |

(52) U.S. Cl.
CPC ............. *G01Q 60/60* (2013.01); *C12Q 1/005* (2013.01); *G01N 33/5438* (2013.01); *G01Q 70/12* (2013.01)

(58) Field of Classification Search
CPC ........ G01Q 60/60; G01Q 70/12; C12Q 1/005; G01N 33/5438

USPC ................ 850/29, 52, 56, 57, 58, 59, 60, 61
See application file for complete search history.

(56) References Cited

U.S. PATENT DOCUMENTS

| | | | |
|---|---|---|---|
| 8,349,604 B2 | 1/2013 | Mohapatra et al. | |
| 8,513,804 B2 | 8/2013 | Hellstrom et al. | |
| 8,966,661 B2 | 2/2015 | Chang et al. | |
| 9,354,205 B2 | 5/2016 | Tseng et al. | |
| 9,638,717 B2 | 5/2017 | Lieber et al. | |
| 9,671,432 B2 | 6/2017 | O'Riordan et al. | |
| 9,689,829 B2 | 6/2017 | Farrow et al. | |
| 9,983,183 B2 | 5/2018 | Motayed et al. | |
| 10,012,674 B2 | 7/2018 | Dill et al. | |
| 10,109,387 B2 | 10/2018 | Mueller-Meskamp et al. | |
| 2012/0122715 A1* | 5/2012 | Gao | G01N 33/5438 422/69 |
| 2013/0143319 A1* | 6/2013 | Yu | C12N 13/00 435/375 |
| 2014/0262433 A1 | 9/2014 | Lim et al. | |

(Continued)

*Primary Examiner* — Nicole M Ippolito
(74) *Attorney, Agent, or Firm* — Whiteford, Taylor & Preston, LLP; Gregory M. Stone

(57) ABSTRACT

Disclosed is a method for preparing nanoscale electrodes comprised of electrochemically grown noble metal nanowires, and use of the same for the detection of extremely small concentrations of molecules. Such nanoscale electrodes provide target molecule release information from submicron areas on the cell surface, significantly increasing the spatial resolution of the target molecule mapping of a cell surface to enable localization of target molecules on the cell surface, which can be critical for the detection of certain cells with different properties in a given group of cells, such as circulating tumor cells.

20 Claims, 4 Drawing Sheets

(56) References Cited

U.S. PATENT DOCUMENTS

2014/0285224 A1\* 9/2014 Albuschies ........... B81B 7/0006
438/49
2015/0361489 A1\* 12/2015 Soper ................ B01L 3/502761
506/4

\* cited by examiner

NANOSCALE SCANNING ELECTROCHEMICAL MICROSCOPY ELECTRODE METHOD

CROSS REFERENCE TO RELATED APPLICATIONS

This application is based upon and claims the benefit of U.S. Provisional Application No. 62/838,474 titled "Nanoscale Scanning Electrochemical Microscopy (SECM) Electrode," filed with the United States Patent & Trademark Office on Apr. 25, 2019, the specification of which is incorporated herein by reference in its entirety.

GOVERNMENT LICENSE RIGHTS

Portions of the invention described herein were made with government support under Contract No. W911NF-12-2-0022 awarded by the U.S. Army, and under Contract No. UL1GM118973 awarded by the National Institutes of Health. The U.S. government may have certain rights in the invention.

FIELD OF THE INVENTION

This invention relates generally to nanoscale electrodes and methods of their fabrication, and more particularly to methods for preparing nanoscale electrodes for selective detection and mapping of target molecules, and methods for using such nanoscale electrodes for the selective detection and mapping of target molecules.

BACKGROUND OF THE INVENTION

Electrodes play a critical role in many applications, including for example in the fields of biosensing, electrically active cell data recording, and corrosion research. Very small scale electrodes find application in scanning electrochemical microscopy (SECM), which is a powerful analytical tool for the identification of local electrochemical processes at various interfaces between gases, liquids, and solids. SECM may be used in the detection and analysis of individual molecules, and efforts to obtain higher fidelity in such detection and analysis is ongoing. Electrode fabrication is one of the most critical tasks in efficient utilization of SECM. Ultramicroelectrodes (UMEs) have been the standard choice of electrodes in most SECM experiments and their charge transfer kinetics have been well characterized. Moreover, there has been increasing interest in using nanoscale electrodes in SECM due to their unique inherent properties. However, their current preparation methods are laborious and not cost-effective, hindering the effective and wide scale use of SECM in nanoscale detection and imaging.

Aptamers are short oligonucleotide chains, which can be designed to bind to target molecules in a highly selective process. SECM electrodes that are currently used in aptamer-based biosensing studies typically have diameters of several microns. While small in scale, such several micron diameter electrodes are nonetheless too large to effectively enable site-specific target molecule detection from a single cell surface.

Efforts have been made to provide small scale, and even nanoscale, probes for various purposes. For example, U.S. Pat. No. 8,349,604 to Mohapatra et al. discloses a nano-based sensor having a nanoscale electrode in a microfluidic device for detection of blood analytes, disease biomarkers, and other target molecules. U.S. Pat. No. 8,513,804 to Hellstrom et al. discloses a transparent electrode coated with a network of carbon nanotubes in a conjugated polymer. U.S. Pat. No. 8,966,661 to Chang et al. discloses a system and method for forming a nanoscale probe through etching of a conductor to form a necking portion, and ultimately forming a nanoscale probe when the first conductor breaks at the necking portion. U.S. Pat. No. 9,354,250 to Tseng et al. discloses a nanoscale probe comprised of a tip and a planar surface, each having a metallic coating layer and an insulating layer. U.S. Pat. No. 9,638,717 to Lieber et al. discloses nanoscale wires for use in sensors where the nanoscale wire is connected to an electrode to form part of a transistor. U.S. Pat. No. 9,671,432 to O'Riordan et al. discloses a sensor device including a nanowire electrode and a faradic shield adapted to prevent unwanted capacitive charging current in the sensor. U.S. Pat. No. 9,689,829 to Farrow et al. discloses a nanoprobe including a first nanotube on a first electrode and a second nanotube on a second electrode, with the separate nanotubes spaced apart by a distance less than a target cell, which nanoprobe determines the presence of a cell by sensing impedance between the two nanotubes. U.S. Pat. No. 9,983,183 to Motayed et al. discloses a nanostructure sensor including a semiconductor nanostructure and nanoparticle clusters forming a photoconductive nanostructure/nanocluster hybrid sensor. U.S. Pat. No. 10,012,674 to Dill et al. discloses a nanoantenna scanning probe tip covered with a film of plasmonic nanoparticles. U.S. Pat. No. 10,109,387 to Mueller-Meskamp et al. discloses a multi-layer transparent electrode that includes an electrically conductive layer containing metal nanowires. Finally, U.S. Patent Application Publication No. 2014/0262433 of Lim et al. discloses a nano electrode having a protruded probe, a nanowire attached to the protruded probe, and an insulating film.

Notwithstanding the foregoing efforts, there remains a need in the art for nanoscale electrodes capable of use in aptamer-based biosensing applications that may offer high resolution detection of target molecules from, and mapping of, a single cell surface in an efficient and cost-effective assembly.

SUMMARY OF THE INVENTION

Disclosed herein is a novel, cost effective method for preparing nanoscale SECM electrodes comprised of electrochemically grown noble metal, such as gold and/or platinum, nanowires. Such nanoscale electrodes may provide highly selective biosensing capabilities in the detection of extremely small concentrations of molecules. Such nanoscale electrodes offer indispensable size advantages, not achievable with the state-of-the-art technology and thus have potential application to not only SECM, but also in a wide range of other applications such as cancer detection, neurological data recording, use as environmental sensors and in pharmaceutical development. By way of non-limiting example, nanoscale electrodes formed and used in accordance with certain aspects of the invention may provide for the detection of target molecule release information from submicron areas on the cell surface, significantly increasing the spatial resolution of the target molecule mapping of a cell surface. Such high-resolution maps may enable localization of target molecules on the cell surface, which can be critical for the detection of certain cells with different properties in a given group of cells, such as circulating tumor cells.

Nanoscale electrodes configured in accordance with at least certain aspects of the invention may thus be used in applications such as nanoscale mapping and highly sensitive detection of biological molecules. Further, methods carried out in accordance with at least certain aspects of the invention may increase spatial resolution of, for example, aptamer-based electrochemical sensing of target molecules from live cells using SECM. Such methods may likewise enable the mapping of a broad range of specific target molecules released from single cell surfaces with very high spatial resolutions that cannot be realized with standard ultramicroelectrodes. The nano-size tips of nanoscale electrodes formed in accordance with such aspects of the invention may likewise enable high-resolution detection of target molecules from a single cell surface, and methods in accordance with such aspects of the invention may lead to the cost-effective fabrication of aptamer-based nanoelectrodes, as minimal quantities of noble metals will be used in their salt forms.

In accordance with certain aspects of an embodiment, a method is provided for detecting the presence of a target molecule on a surface of a cell, comprising: providing a pair of tapered-tip electrodes; placing a tip of each tapered-tip electrode in a saturated solution of a noble metal salt; applying an electrical potential between the tips to grow a nanowire formed of the noble metal in the saturated solution, the nanowire having a first end affixed to one of the tapered-tip electrodes and a second, free end opposite the first end; attaching an aptamer to the second, free end of the nanowire; applying the second, free end of the nanowire to a single cell; and recording an electronic signal from the nanowire indicative of the presence of a target molecule on the single cell having a binding affinity with the aptamer on the second, free end of the nanowire.

In accordance with further aspects of an embodiment, a method is provided for forming a nanowire electrode configured for the detection of the presence and location of a single molecule on a surface of a cell, comprising the steps of: providing a pair of tapered-tip electrodes; placing a tip of each of the tapered-tip electrodes in a saturated solution of a noble metal salt; applying an electrical potential between the tips to grow a nanowire formed of the noble metal in the saturated solution, the nanowire having a first end affixed to one of the tapered-tip electrodes and a second, free end opposite the first end, and wherein the nanowire has a diameter of not greater than 100 nm; and attaching an aptamer to the second, free end of the nanowire.

In accordance with still further aspects of an embodiment, a nanowire configured for detecting the presence of a target molecule on a surface of a cell is provided, comprising: a tapered-tip electrode; a nanowire formed of a noble metal affixed to the tapered-tip electrode, wherein the nanowire has a diameter of not greater than 100 nm; a glass insulator surrounding the tapered-tip electrode and the nanowire, wherein an end of the nanowire extends outside of the glass insulator; and an aptamer attached to the end of the nanowire, wherein the aptamer is selected for having a binding affinity to a target molecule on the surface of a cell.

BRIEF DESCRIPTION OF THE DRAWINGS

The numerous advantages of the present invention may be better understood by those skilled in the art by reference to the accompanying drawings in which.

DETAILED DESCRIPTION

Figure 1:
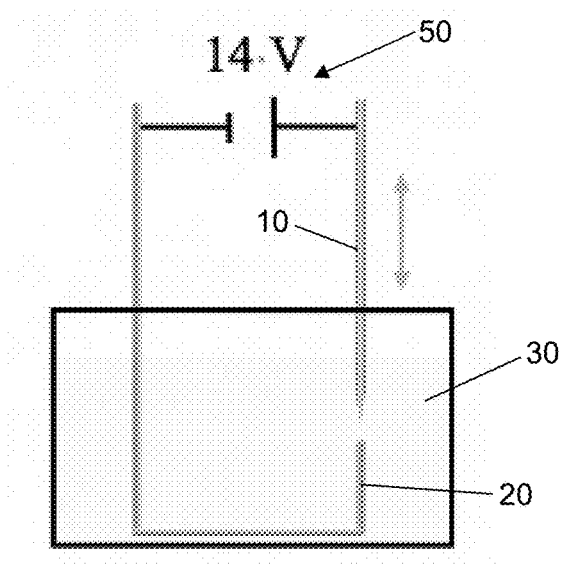
FIG. 1 is a schematic view of an assembly for forming tapered-tip electrodes in accordance with certain aspects of an embodiment of the invention.

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

In accordance with certain aspects of an embodiment of the invention, a method of forming nanoscale electrodes is provided, which nanoscale electrodes are configured for use in nanoscale mapping and highly sensitive detection of biological molecules using SECM. Such SECM nanoscale electrodes are comprised of metallic nanowires, such as gold or platinum, which are grown from tapered sharp tungsten electrodes using Directed Electrochemical Nanowire Assembly (DENA) as described in further detail below. Such method enables simple diameter tuning of nanowires and their direct interfacing with tungsten wires, enabling a facile electrode preparation method. Methods performed in accordance with certain aspects of the invention may provide cost savings over previously known methods, as salt solutions of target noble metals are used in growing nanowires directly from tapered tungsten wires. The selective detection of a target molecule may be achieved by attaching aptamers, such as DNA aptamers, on the surface of an electrode formed in accordance with certain aspects of the invention. The aptamers may be terminated with an oxidation-reduction indicator (i.e., a "redox indicator"), such as (by way of non-limiting example) Methylene Blue (MB) redox molecules, and an electronic signal may be recorded with standard voltammetry due to target induced conformal changes in the aptamer. Such MB tagged aptamers will experience conformal change on the electrode surface upon binding to the target molecule, moving the MB molecule closer to the electrode tip and causing the reduction of the MB signal, which in turn will be detected by the SECM.

While the exemplary embodiment described herein particularly employs DNA aptamers attached to the surface of an electrode formed in accordance with certain aspects of the invention, it is envisaged that other aptamers may likewise be employed. For example, RNA aptamers, X-aptamers, and peptide aptamers may likewise be employed using the principles set forth herein without departing from the spirit and scope of the invention.

With reference to the schematic view of FIG. 1, tapered sharp tungsten electrodes are prepared. More specifically, 0.25 mm diameter annealed tungsten wires are electrochemically etched to obtain tapered tip electrodes for nanowire growth. A 14 volt DC potential 50 is applied between a tungsten wire 10 and a counter electrode 20 in two molar sodium hydroxide solution 30. Tungsten wires 10 were manually immersed in and removed from the solution 30 at about 1 Hz frequency during the etching process until visually sharp and tapered electrodes were obtained. The smallest diameter of the resulting etched tungsten wire is preferably no greater than 2 µm, and more preferably no greater than approximately 1 µm. In varying operable configurations, the etched tungsten wires may have a radius of curvature of up to about 10 µm while still maintaining precise control over localizing the location of nanowire growth on the tip of the tungsten wire 10.

Figure 2:
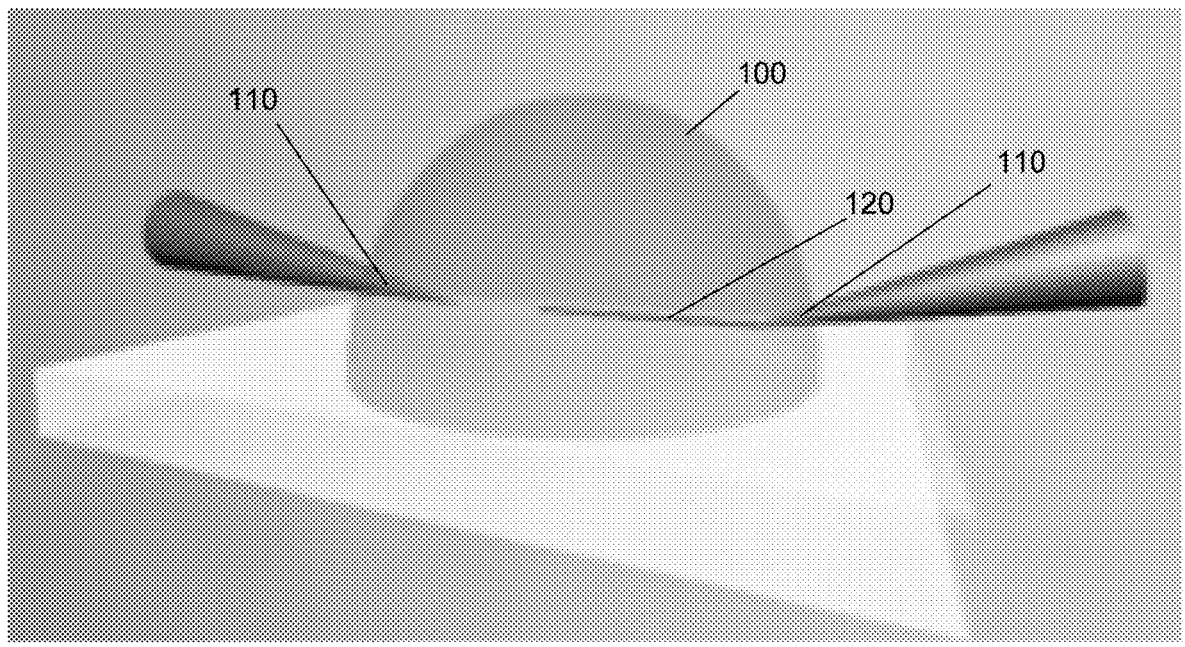
FIG. 2 is a diagrammatic view of the formation of a nanowire electrode in accordance with certain aspects of an embodiment of the invention.

With reference to FIG. 2, a saturated solution 100 of a target material, in an exemplary embodiment gold chloride, was deposited between a pair of tapered tungsten electrodes 110 formed as above for the growth of an individual nanowire 120. The nanowire 120 grows with the application of high frequency potential for the growth of an individual nanowire. In certain configurations, the nanowire 120 grows with the application of high frequency (such as by way of non-limiting example, over 20 MHz) square wave AC potential from one electrode to the counter electrode. While the exemplary embodiment employed an optimal frequency of at least 20 MHz, other frequencies of approximately 10 MHz, and while less preferable even as low as 5 MHz, may likewise be employed while still maintaining the ability to initiate nanowire growth.

Figure 3:
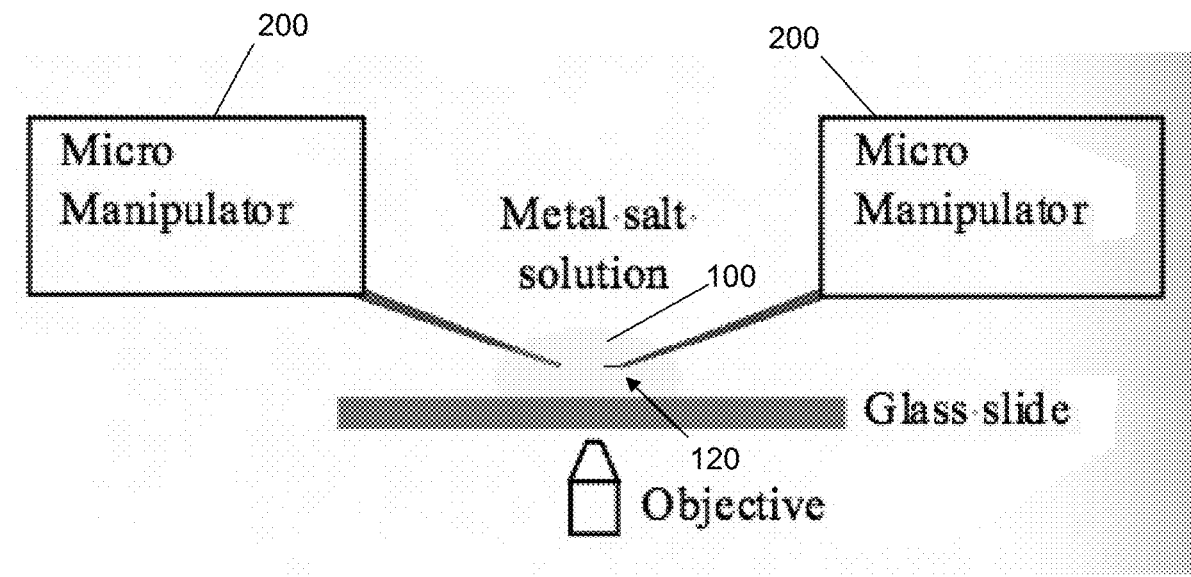
FIG. 3 is a further diagrammatic view of the formation of a nanowire electrode in accordance with certain aspects of an embodiment of the invention.

As shown in FIG. 3, a high degree of control over the position of an individual nanowire 120 is also feasible as the nanowire growth can be paused before reaching the counter electrode and the nanowire 120 can be moved on to any substrate of choice with micromanipulators 200 for further characterization.

Nanowires 120 grown using the methods described above and in accordance with aspects of the invention were determined to be purely metallic, although other moieties are present in the solution 100, indicating that only cations are deposited during wire growth. Furthermore, the foregoing method for forming a nanoscale electrode was identified as a dendritic solidification process. The applied voltage frequency dependence of DENA growth parameters, such as growth velocity and wire diameter, were shown to be in good agreement with the solution of the diffusion equation:

$$\partial c(r,t)/\partial t = -\nabla \cdot \vec{j}$$

where $c(r,t)$ is the concentration profile and $\vec{j}$ is the flux of the cations.

The growth of individual alloy nanowires 120 is also potentially possible by mixing stock solutions, and such nanowires are expected to demonstrate novel properties. Moreover, DENA allows simple tuning of nanowire diameters by changing the frequency of the applied AC potential and the concentration of the salt solution 100. DENA grown gold nanowire diameters were reduced to ~45 nm by controlling the AC growth frequency and the salt solution concentration. As the nanowire diameters and their tip radius of curvature are correlated, the facile diameter control property of the DENA method may play a key role in determining the optimized size parameters of nanowire electrodes 120 for obtaining high resolution target molecule maps.

Importantly, in addition to reducing the radius of curvatures of the tips of nanowire electrodes 120, the foregoing methods may also substantially reduce the consumption of noble metals, such as gold and platinum, making the methods of forming nanoscale electrodes 120 in accordance with certain aspects of the invention significantly cost effective. This may be achieved by replacing the bulk wire forms of the noble metals in the standard electrode preparation methods with electrochemically grown nanowires of the same metals (gold and platinum) from their salt solutions, as discussed above. Moreover, such nanowire electrodes 120 were grown from sharp, tapered tungsten wires, which are also significantly cost effective compared to noble metals. The efficiency of nanowire electrodes 120 formed in accordance with aspects of the invention was tested by comparing the resolution of the target molecule maps to the existing standard electrodes, which are prepared by pulling metal nanowires inserted in micropipettes.

Figure 4:
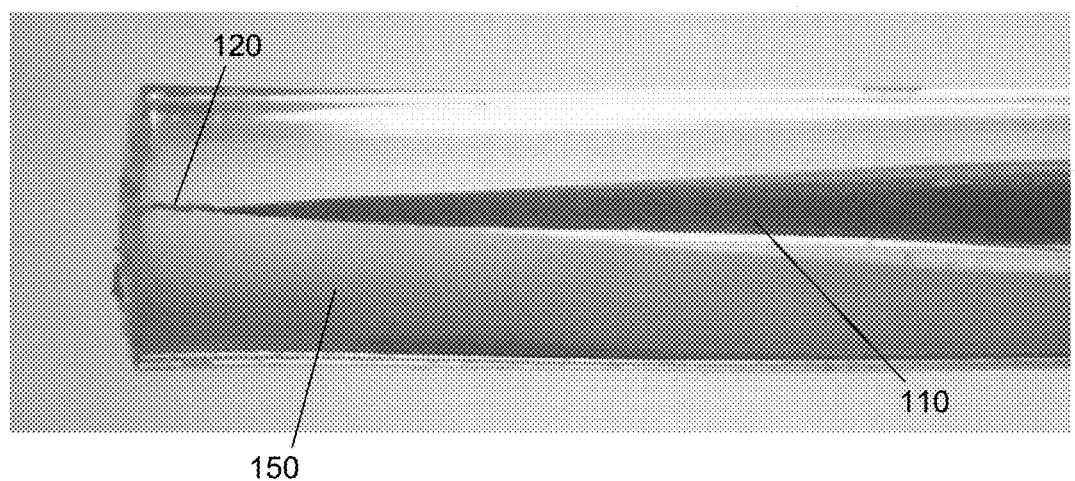
FIG. 4 is a close-up side view photograph of an insulated nanoelectrode formed in accordance with certain aspects of an embodiment of the invention.

Insulation of nanowire electrodes 120 can be an important step to obtain controlled surface area exposed tips on those electrodes 120, enabling operation of the nanowire electrodes 120 with reduced noise and capacitance. FIG. 4 provides a side-view photograph of a glass insulated nanoscale electrode 120, fabricated with a noble metal, such as gold, nanowire electrode 120 on the tip of a tungsten wire 110 that has been etched as described above and placed within a section of borosilicate capillary glass 150. The tip of the nanowire electrode 120 may be exposed by sanding and polishing the nanowire end of the glass insulated electrode assembly.

The electroactive surface areas of the fabricated nanowire electrodes 120 were determined with the following equation: $I_c = 2AC_e v$, where $I_c$ is the charge current, A is the surface area, $C_e$ is the capacitance of the electrode 120, and v is the scan rate. Electrochemical characteristics of the insulated nanowire electrodes 120 were tested in standard solution, such as potassium ferricyanide, by recording steady state voltammetric responses. Picoamp level charge currents indicate the achievement of well-insulated electrodes with nanoscale tips. The following standard equation was used in verifying the tip geometries of the nanowire electrodes 120 formed in accordance with certain features of the invention based on the measured steady-state currents:

$$I_{\tau,\infty} = knFDCa$$

where $k=4$ for disc and $k=2\pi$ for hemisphere tip geometry, I is the measured steady-state current, n is the number of electrons involved in the redox reaction, F is the Faraday constant, D is the diffusion coefficient of the redox species, C is the bulk concentration of the species, and a is the electroactive surface radius.

As mentioned above, nanowire electrodes 120 formed in accordance with the foregoing methods may be used for the selective detection of target molecules, and in fact may provide for greater spatial resolution of, for example, aptamer-based electrochemical sensing of target molecules from live cells using SECM. Such nanowire electrodes 120 may also enable the mapping of a broad range of specific target molecules released from single cell surfaces with very high spatial resolutions that cannot be realized with standard ultramicroelectrodes. The nano-size tips of nanowire electrodes 120 formed in accordance with certain aspects of the invention may enable high resolution detection of target molecules from a single cell surface. In an exemplary implementation, aptamers (such as DNA aptamers) are attached to the surface of nanowire electrodes 120. Those aptamers are preferably terminated with, for example, Methylene Blue (MB) redox molecules, and an electronic signal is recorded with standard voltammetry due to target induced conformal changes in the aptamer. The nanowire electrodes 120 with aptamers attached as described here were successfully used in the detection of picomolar concentration Adenosine triphosphate (ATP) molecules. In certain implementations, the aptamer-coated electrodes may be further backfilled by small thiol molecules, such as 6-mercapto-1-hexanol (6-MCH) to avoid non-specific adsorption of target molecules to the electrode surface. In use, MB-tagged aptamers will move closer to the electrode surface upon binding to the target molecule, causing the reduction of the MB signal which will be detected by the SECM.

Figure 5:
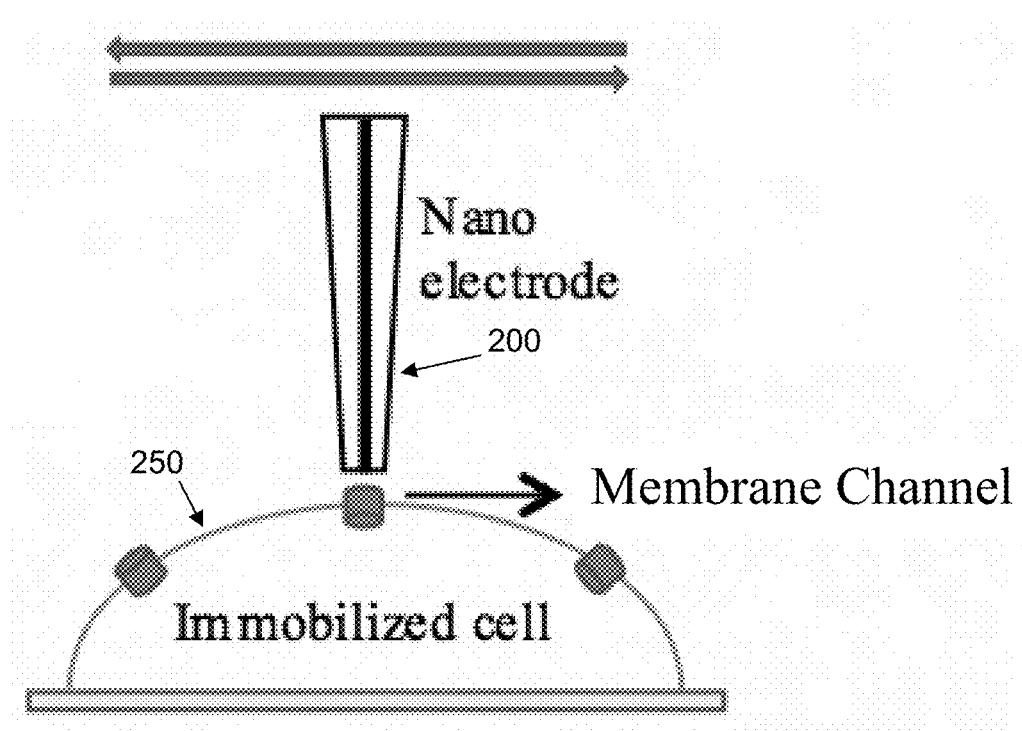
FIG. 5 is a diagrammatic view of a system for mapping the locations of molecules on the surface of a call using an insulated nanoelectrode in accordance with certain aspects of an embodiment of the invention.

With reference to FIG. 5, insulated nanowire electrodes (shown generally at 200) formed in accordance with the foregoing (and comprising tapered-tip electrode 110, nanowire 120, and insulator 150 all as described above) may provide target molecule release information from submicron areas on the cell surface 250, significantly increasing the spatial resolution of the target molecule mapping of a cell surface. Such high-resolution maps may enable localization of target molecules on the cell surface, which may be critical for the detection of certain cells with different properties in a given group of cells, such as Circulating Tumor Cells ("CTCs").

As an example, nanowire electrodes 120 can aid in the detection of vimentin, an intermediate filament protein, which is overexpressed in pancreatic, breast, and other cancer cells. NAS-24 aptamer may be used in selective binding to vimentin release from cancer cell surfaces and submicron, high spatial resolution maps can be obtained from a single cell surface.

Figure 6:
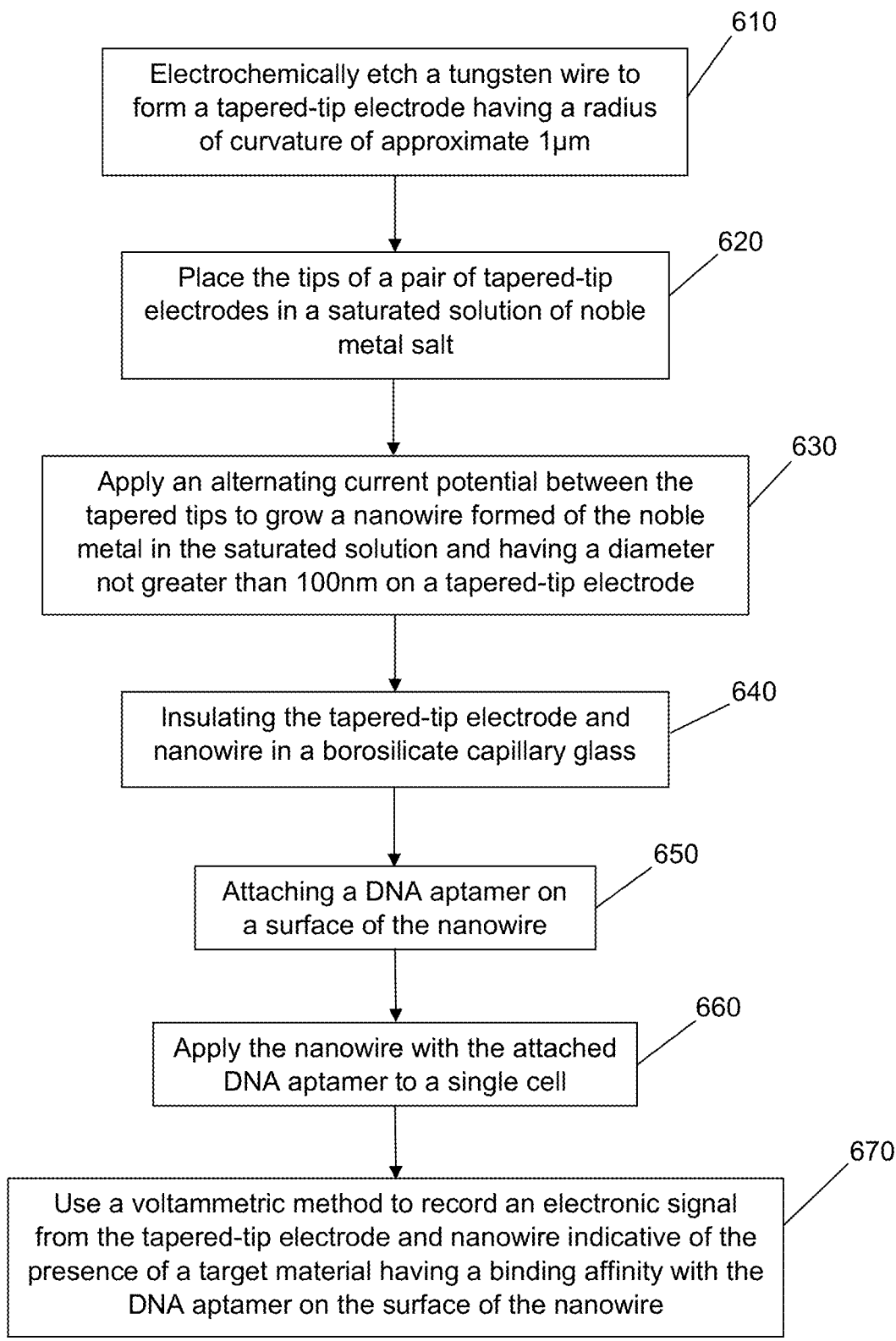
FIG. 6 is a flowchart depicting a method for forming a nanoelectrode and using the same to detect the presence, and ultimately location, of target molecules on the surface of a single cell in accordance with certain aspects of an embodiment of the invention.

FIG. 6 is a flowchart representing an exemplary method in accordance with the foregoing and certain aspects of an embodiment of the invention. At step 610, metal wires, such as tungsten wires, are electrochemically etched to form a tapered-tip electrode having a radius of curvature of approximately 1 μm. At step 620, the tips of a pair of tapered-tip electrodes 110 formed as at step 610 are placed in a saturated solution of a noble metal salt 100, such as gold chloride. At step 630, an alternating current potential is applied between the tapered tips of the tapered-tip electrodes 110 to grow a nanowire 120 on the tapered tip electrode, and having a diameter that is preferably not greater than 100 nm. At step 640, a combined tapered-tip electrode with an attached nanowire is insulated in, for example, borosilicate capillary glass, to form insulated nanowire electrode 200. At step 650, an aptamer, such as by way of non-limiting example a DNA aptamer, is attached on a surface of the nanowire 120 of insulated nanowire electrode 200. At step 660, the exposed nanowire tip of insulated nanowire electrode 200 with the attached aptamer is applied to a single cell. At step 670, a voltammetric method (which methods are well known to those of ordinary skill in the field of analytical chemistry and are thus not further detailed here) is used to record an electronic signal from the insulated nanowire electrode 200, which electronic signal is indicative of the presence of a target material having a binding affinity with the aptamer on the surface of the nanowire.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A method for detecting the presence of a target molecule on a surface of a cell, comprising:
    providing a pair of tapered-tip electrodes;
    placing a tip of each of said tapered-tip electrodes in a saturated solution of a noble metal salt;
    applying an electrical potential between said tips to grow a nanowire formed of the noble metal in the saturated solution, said nanowire having a first end affixed to one of said tapered-tip electrodes and a second, free end opposite said first end;
    attaching an aptamer to said second, free end of the nanowire;
    applying said second, free end of said nanowire to a single cell; and
    recording an electronic signal from the nanowire indicative of the presence of a target molecule on the single cell having a binding affinity with the aptamer on the second, free end of the nanowire.

2. The method of claim 1, wherein said nanowire has a diameter of not greater than 100 nm.

3. The method of claim 1, further comprising repeating said applying and recording steps on said single cell to determine the locations of multiple target molecules on a surface of said single cell.

4. The method of claim 1, further comprising the step of forming said tapered-tip electrodes by electrochemically etching a pair of metal wires.

5. The method of claim 4, wherein said metal wires comprise tungsten.

6. The method of claim 4, wherein said tapered-tip electrodes are electrochemically etched to produce said tapered tips having a minimum diameter of no greater than 2 μm.

7. The method of claim 1, wherein said step of applying an electrical potential further comprises applying an alternating current potential having a frequency of at least 5 MHz.

8. The method of claim 7, wherein said alternating current potential further comprises a square wave alternating current potential.

9. The method of claim 1, further comprising the step of placing said one of said tapered-tip electrodes and said nanowire inside of a glass insulator.

10. The method of claim 9, wherein said glass insulator further comprises borosilicate capillary glass.

11. The method of claim 9, further comprising the step of exposing said second, free end of said nanowire by sanding and polishing and end of said glass insulator to form a glass insulated nanowire electrode.

12. The method of claim 1, further comprising the step of terminating the aptamer with a redox indicator.

13. The method of claim 1, wherein the noble metal salt further comprises gold chloride.

14. A method of forming a nanowire electrode configured for the detection of the presence and location of a single molecule on a surface of a cell, comprising the steps of:
providing a pair of tapered-tip electrodes;
placing a tip of each of said tapered-tip electrodes in a saturated solution of a noble metal salt;
applying an electrical potential between said tips to grow a nanowire formed of the noble metal in the saturated solution, said nanowire having a first end affixed to one of said tapered-tip electrodes and a second, free end opposite said first end, and wherein said nanowire has a diameter of not greater than 100 nm; and
attaching an aptamer to said second, free end of the nanowire.

15. The method of claim 14, further comprising the step of forming said tapered-tip electrodes by electrochemically etching a pair of tungsten wires to produce said tapered tips having a minimum diameter of no greater than 2 µm.

16. The method of claim 14, wherein said step of applying an electrical potential further comprises applying a square wave alternating current potential having a frequency of at least 5 MHz.

17. The method of claim 14, further comprising the steps of placing said one of said tapered-tip electrodes and said nanowire inside of a glass insulator, and exposing said second, free end of said nanowire by sanding and polishing and end of said glass insulator to form a glass insulated nanowire electrode.

18. The method of claim 14, further comprising the step of terminating the aptamer with a redox indicator.

19. The method of claim 14, wherein the noble metal salt further comprises gold chloride.

20. A nanowire configured for detecting the presence of a target molecule on a surface of a cell, comprising:
a tapered-tip electrode;
a nanowire formed of a noble metal affixed to said tapered-tip electrode, wherein said nanowire has a diameter of not greater than 100 nm;
a glass insulator surrounding said tapered-tip electrode and said nanowire, wherein an end of said nanowire extends outside of said glass insulator; and
an aptamer attached to said end of said nanowire, wherein said aptamer is selected for having a binding affinity to a target molecule on the surface of a cell.

* * * * *